US008710194B2

(12) United States Patent
Picci et al.

(10) Patent No.: US 8,710,194 B2
(45) Date of Patent: Apr. 29, 2014

(54) SINGLE-CHAIN VARIABLE FRAGMENT (SCFV) ABLE TO RECOGNIZE AND BIND CD99 HUMAN PROTEIN

(75) Inventors: Piero Picci, San Lazzaro di Savena (IT); Katia Scotlandi, Bologna (IT); Alessandro Ascione, Rome (IT); Maurizio Cianfriglia, Anzio (IT); Maria Luisa Dupuis, Rome (IT); Michela Flego, Rome (IT); Mara Gellini, Rome (IT); Alessandra Mallano, Rome (IT)

(73) Assignee: Istituto Ortopedico Rizzoli, Bologna (IL)

( * ) Notice: Subject to any disclaimer, the term of this patent is extended or adjusted under 35 U.S.C. 154(b) by 0 days.

(21) Appl. No.: 13/509,276

(22) PCT Filed: Nov. 12, 2010

(86) PCT No.: PCT/IB2010/055135
§ 371 (c)(1),
(2), (4) Date: Jul. 10, 2012

(87) PCT Pub. No.: WO2011/058517
PCT Pub. Date: May 19, 2011

(65) Prior Publication Data
US 2012/0282257 A1 Nov. 8, 2012

(30) Foreign Application Priority Data
Nov. 13, 2009 (IT) .............................. MI2009A1994

(51) Int. Cl.
*C07K 16/30* (2006.01)
*A61K 39/395* (2006.01)

(52) U.S. Cl.
USPC ................ 530/388.85; 530/387.3; 530/387.7; 530/388.22; 530/388.8; 424/133.1; 424/135.1; 424/138.1; 424/143.1; 424/155.1; 536/23.53; 435/320.1; 435/325

(58) Field of Classification Search
CPC ........... A61K 39/395; A61K 39/39558; A61K 2039/505; C07K 16/30; C07K 16/2896; C07K 2317/24; C07K 2317/50; C07K 2317/622; C07K 2317/626; C07K 2316/95
See application file for complete search history.

(56) References Cited

FOREIGN PATENT DOCUMENTS

WO 2007/037601 A1 4/2007

OTHER PUBLICATIONS

Paul, Fundamental Immunology, 3rd Edition, 1993, pp. 292-295.*
Muyldermans, Rev Mol Biotech 2001; 74:277-302.*
Rudikoff et al., Proc. Nat'l Acad. Sci. USA 1982; 79:1979-83.*
Brown et al., J. Immunol. May 1996; 156(9):3285-91.*
Tsurushita et al., Methods, 2005; 36:69-83.*
Dall'Acqua et al., Methods 2005; 36:43-60.*
Chan and Carter, Nature Reviews Immunology, 2010; 10:301-316.*
Cragg et al., Br. J Cancer 1999; 79:850-57.*
Anderson et al., Expert Opin Investig Drugs 2008: 17(11):1703-1715.*
Khunkaewla et al., Hybridoma 2007; 26(4):241-248.*
Vitetta & Ghetie, Science 2006; 313:308-09.*
Brand et al., Anticancer Res. 2006; 26:463-70.*
Weisser et al., Biotech Adv 2009; 27-502-520.*
Search Report of Italian Application MI2009001994 filed Nov. 13, 2009 in the name of Istituto Ortopedico Rizzoli, Completion Date: Jun. 16, 2010.
Written Opinion of Italian Application MI2009001994 filed Nov. 13, 2009 in the name of Istituto Ortopedico Rizzoli, Completion Date: Jun. 16, 2010.
PCT Search Report of International Application PCT/IB2010/055135 filed Nov. 12, 2010 in the name of Istituto Ortopedico Rizzoli, Mail Date: Mar. 11, 2011.
PCT Written Opinion of International Application PCT/IB2010/055135 filed Nov. 12, 2010 in the name of Istituto Ortopedico Rizzoli, Mail Date: Mar. 11, 2011.
Progetto alleanza contro il cancro 2007-2009 Programma 3 Sviluppo di nuove terapie nei sarcomi muscolo scheletrici: immunoterapia e target terapia a confronto. Retrieved from the internet [url: www.alleanzacontroilcancro.it/binary/acca/cont/picci.1211368425.pdf] on Jun. 11, 2010. (Cited in International Search Report).
Monoclonal Mouse Anti-Human CD99, Ewing's Sarcoma Marker MIC2 Gene Products, Clone 12E7 (Codice N1593). Retrieved from the internet [url: http://www.dako.it/prod_downloadpackageinsert.pdf?objectid=109776002] on Jun. 11, 2010. (Cited in International Search Report), Mar. 2007.
S. Perdichizzi. Identificazione del ruolo biologico e funzionale della forma maggiore e della forma troncata della proteina CD99 (p20/32 mic2) e potenzialità terapeutiche nel sarcoma di Ewing. Retrieved from the internet [url: http://www.patologia-sperimentale.unibo.it/Dottorato/tesi_libere/tesi_perdichizzi.pdf] on Jun. 11, 2010 (Cited in International Search Report), Academic year 2003-2004.
K. Scotlandi. Targeted therapies in Ewing's sarcoma. Adv. Exp. Med. Biol., vol. 587, pp. 13-22; 2006 [Abstract Only].
K. Scotlandi, et al. Targeting CD99 in association with doxorubicin: An effective combined treatment for Ewing's sarcoma. European Journal of Cancer, vol. 42, No. 1, pp. 91-96, Jan. 1, 2006.
K. Scotlandi, et al. CD99 engagement: an effective therapeutic strategy for Ewing tumors. Cancer Research, vol. 60, No. 18, pp. 5134-5142, Sep. 15, 2000.
A. Rocchi, et al. CD99 inhibits neural differentiation of human Ewing sarcoma cells and thereby contributes to oncogenesis. Journal of Clinical Investigation, vol. 120, No. 3, pp. 668-680, Mar. 2010.

(Continued)

*Primary Examiner* — Sheela J Huff
*Assistant Examiner* — Jessica H Roark
(74) *Attorney, Agent, or Firm* — Lucas & Mercanti, LLP

(57) ABSTRACT

The present invention relates to a single-chain variable fragment (scFv) able to recognize an epitope of the extracellular domain of CD99 human protein. The single-chain variable fragment is able to recognize and specifically and selectively bind the epitope of the extracellular domain of CD99 human protein expressed on Ewing sarcoma cells. The fragment can thus be used for the diagnosis and 10 treatment of Ewing sarcoma.

26 Claims, 4 Drawing Sheets

(56) References Cited

OTHER PUBLICATIONS

Subbiah V, Anderson P, Lazar AJ, Burdett E, Raymond K, Ludwig JA.Ewing's sarcoma: standard and experimental treatment options. Curr Treat Options Oncol 10, 126-140 (2009). Abstract Only.

Picci P, Scotlandi K, Serra M, Rizzi A. Prognostic and therapeutic targets in the Ewing's family of tumors (Prothets). Adv Exp Med Biol. 587, 1-12 (2006). Abstract Only.

Alberti I, Bernard G, Rouquette-Jazdanian AK, Pelassy C, Pourtein M, Aussel C and Bernard A. CD99 isoforms expression dictates T cell functional outcomes. FASEB J; 16: 1946-1948 (2002).

Mirick GR, Bradt BM, Denardo SJ, Denardo GL: A review of human anti-globulin antibody (HAGA, HAMA, HACA, HAHA) responses to monoclonal antibodies. Not four letter words. Q J Nucl Med Mol Imaging.; 48 (4) : 251-7 (2004).

Liu XY, Pop LM, Vitetta ES: Engineering therapeutic monoclonal antibodies. Immunol Rev.; 222: 9-27 (2008).

Hinoda Y, Sasaki S, Ishida T, Imai K : Monoclonal antibodies as effective therapeutic agents for solid tumors. Cancer Sci. 2004; 95(8) :621-5.

Lanzavecchia A: Human monoclonal antibodies by immortalization o f memory B cells. Curr Opin Biotechnol. 2007; 18(6) :523-8.

Carter PJ: Potent antibody therapeutics by design. Nat Rev Immunol. 2006; 6(5) :343-57.

Hoogenboom H: Selecting and screening recombinant antibody libraries. Nat Biotechnol. 2005; 23(9) :1105-16.

Holliger P, Hudson PJ: Engineered antibody fragments and the rise of single domains. Nat Biotechnol. 2005; 23(9): 1126-36.

Sharkey RM and Goldenberg DM: Immunoconjugates Targeted Therapy of Antibodies and cancer. Cancer: New Prospects for CA Cancer J Clin. 2006; 56; 226-243.

Pavoni E, Flego M, Dupuis ML, Barca S, Petronzelli F, Anastasi AM, D' Ale s sio V, Pelliccia A, Vaccaro P, Monteriu G, Ascione A, De Santis R, Fe lici F, Cianfriglia M, Minenkova O. Selection, affinity maturation, and characterization of a human scFv antibody against CEA protein. BMC Cancer 2006; 6 :41-52.

Kyeong CJ, Nam HK, Weon SP, Seong HP, Youngmee B: The CD99 signal enhances Fas-mediated apoptosis in the human leukemie cell line, Jurkat. FEBS Letters 2003; 554: 478-484.

Viti F, Nilsson F, Demartis S, Huber A, and Neri D: Design and use of phage display libraries for the selection of antibodies and enzymes. Methods Enzimol 2000; 326:480-505.

Ames RS, Tornetta MA, Jones CS, and Ping Tsui: Isolation of neutralizing anti-C5a monoclonal antibodies from a filamentous phage monovalent Fab display library. Journal of Immunology 1994; 152: 4572-4581.

Stausbol-Gron B ,Wind T, Kjer S, Kahns L, Hansen N, Kristensen P, Clark B: A model phage display subtraction method with potential for analysis of differential gen e expression. FEBS Letters 1996; 391: 71-75.

De Kruif J, Boel and Logtenterg T: Selection and application of human single-chain Fv antibody fragments from a semi-synthetic phage antibody display library with designed CDR3 regions. J. Mol. Biol. 1995; 248: 97-105.

Carter P: Improving the efficacy of antibody-based cancer therapies. Nat Rev Cancer 2001; 1(2): 118-29.

Mara Gellini et al., Generation of Human Single-chain Antibody to the CD99 Cell Surface Determinant Specifically Recognizing Ewing's Sarcoma Tumor Cells, Current Pharmaceutical Biotechnology, 2013, vol. 14, No. 4, 15 pages.

* cited by examiner

A

| Ciclo | In | Out | O/I | Arricchimento |
|---|---|---|---|---|
| 1 | $5 \times 10^{12}$ | $3,1 \times 10^4$ | $6,2 \times 10^{-9}$ | 1 |
| 2 | $1 \times 10^{12}$ | $7,6 \times 10^6$ | $7,6 \times 10^{-6}$ | 245 |
| 3 | $1 \times 10^{12}$ | $1,4 \times 10^7$ | $1,4 \times 10^{-5}$ | 451 |
| 4 | $1 \times 10^{12}$ | $1 \times 10^9$ | $1 \times 10^{-3}$ | 32258 |

B

| | CD99-GST I | CD99-GST II | CD99-GST III | CD99-GST IV |
|---|---|---|---|---|
| CD99/His | 0,0125 | 0,0105 | 0,0405 | 0,205 |
| CD99/GST | 0,011 | 0,01 | 0,19 | 0,54 |
| GST | 0,012 | 0,0115 | 0,0285 | 0,0145 |
| CD99/Fc | 0,012 | 0,012 | 0,39 | 0,49 |

SEQUENCE LISTING

```
<160> NUMBER OF SEQ ID NOS: 27

<210> SEQ ID NO 1
<211> LENGTH: 9
<212> TYPE: PRT
<213> ORGANISM: Artificial
<220> FEATURE:
<223> OTHER INFORMATION: CDR3 amino acid sequence of VH Chain

<400> SEQUENCE: 1

Ala Lys Ser His Lys Arg Phe Asp Tyr
1               5

<210> SEQ ID NO 2
<211> LENGTH: 11
<212> TYPE: PRT
<213> ORGANISM: Artificial
<220> FEATURE:
<223> OTHER INFORMATION: CDR3 amino acid sequence of VL Chain

<400> SEQUENCE: 2

Asn Ser Ser Phe Pro Arg Thr Ser Ser Val Val
1               5                   10

<210> SEQ ID NO 3
<211> LENGTH: 10
<212> TYPE: PRT
<213> ORGANISM: Artificial
<220> FEATURE:
<223> OTHER INFORMATION: CDR1 amino acid sequence of VH Chain

<400> SEQUENCE: 3

Gly Phe Thr Phe Ser Ser Tyr Ala Met Ser
1               5                   10

<210> SEQ ID NO 4
<211> LENGTH: 9
<212> TYPE: PRT
<213> ORGANISM: Artificial
<220> FEATURE:
<223> OTHER INFORMATION: CDR2 amino acid sequence VH Chain

<400> SEQUENCE: 4

Ala Ile Ser Gly Ser Gly Gly Ser Thr
1               5

<210> SEQ ID NO 5
<211> LENGTH: 11
<212> TYPE: PRT
<213> ORGANISM: Artificial
<220> FEATURE:
```

<223> OTHER INFORMATION: CDR1 amino acid sequence VL Chain

<400> SEQUENCE: 5

Gln Gly Asp Ser Leu Arg Ser Tyr Tyr Ala Ser
1               5                   10

<210> SEQ ID NO 6
<211> LENGTH: 7
<212> TYPE: PRT
<213> ORGANISM: Artificial
<220> FEATURE:
<223> OTHER INFORMATION: CDR2 amino acid sequence VL Chain

<400> SEQUENCE: 6

Gly Lys Asn Asn Arg Pro Ser
1               5

<210> SEQ ID NO 7
<211> LENGTH: 118
<212> TYPE: PRT
<213> ORGANISM: Artificial
<220> FEATURE:
<223> OTHER INFORMATION: VH Chain amino acid sequence

<400> SEQUENCE: 7

Met Ala Glu Val Gln Leu Val Glu Ser Gly Gly Gly Leu Val Arg Pro
1               5                   10                  15

Gly Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu Glu
            35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser His Lys Arg Phe Asp Tyr Trp Gly Gln Gly Thr
            100                 105                 110

Leu Val Thr Val Ser Arg
        115

<210> SEQ ID NO 8
<211> LENGTH: 109
<212> TYPE: PRT
<213> ORGANISM: Artificial
<220> FEATURE:
<223> OTHER INFORMATION: VL Chain amino acid sequence

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Phe Pro Arg Thr Ser Ser

```
                    85                  90                  95
Val Val Phe Gly Gly Gly Thr Lys Leu Thr Val Leu Gly
                100                 105

<210> SEQ ID NO 9
<211> LENGTH: 14
<212> TYPE: PRT
<213> ORGANISM: Artificial
<220> FEATURE:
<223> OTHER INFORMATION: Linker animo acid sequence

<400> SEQUENCE: 9

Gly Gly Gly Gly Ser Gly Gly Gly Ser Gly Gly Gly Gly
1               5                   10

<210> SEQ ID NO 10
<211> LENGTH: 241
<212> TYPE: PRT
<213> ORGANISM: Artificial
<220> FEATURE:
<223> OTHER INFORMATION: scFv amino acid sequence

<400> SEQUENCE: 10

Met Ala Glu Val Gln Leu Val Glu Ser Gly Gly Gly Leu Val Arg Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser His Lys Arg Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Phe Pro
    210                 215                 220

Arg Thr Ser Ser Val Val Phe Gly Gly Gly Thr Lys Leu Thr Val Leu
225                 230                 235                 240

Gly

<210> SEQ ID NO 11
<211> LENGTH: 27
<212> TYPE: DNA
<213> ORGANISM: Artificial
```

```
<220> FEATURE:
<223> OTHER INFORMATION: CDR3 nucleotide sequence of VH Chain

<400> SEQUENCE: 11
gcgaaatcgc ataagcgttt tgactac                                              27

<210> SEQ ID NO 12
<211> LENGTH: 33
<212> TYPE: DNA
<213> ORGANISM: Artificial
<220> FEATURE:
<223> OTHER INFORMATION: CDR3 nucleotide sequence of VL Chain

<400> SEQUENCE: 12
aactcctctt ttccccggac ttcttctgtg gta                                       33

<210> SEQ ID NO 13
<211> LENGTH: 30
<212> TYPE: DNA
<213> ORGANISM: Artificial
<220> FEATURE:
<223> OTHER INFORMATION: CDR1 nucleotide sequence of VH Chain

<400> SEQUENCE: 13
ggattcacct ttagcagcta tgccatgagc                                           30

<210> SEQ ID NO 14
<211> LENGTH: 27
<212> TYPE: DNA
<213> ORGANISM: Artificial
<220> FEATURE:
<223> OTHER INFORMATION: CDR2 nucleotide sequence of VH Chain

<400> SEQUENCE: 14
gctattagtg gtagtggtgg tagcaca                                              27

<210> SEQ ID NO 15
<211> LENGTH: 36
<212> TYPE: DNA
<213> ORGANISM: Artificial
<220> FEATURE:
<223> OTHER INFORMATION: CDR1 nucleotide sequence of VL Chain

<400> SEQUENCE: 15
tgccaaggag acagcctcag aagctattat gcaagc                                    36

<210> SEQ ID NO 16
<211> LENGTH: 21
<212> TYPE: DNA
<213> ORGANISM: Artificial
<220> FEATURE:
<223> OTHER INFORMATION: CDR2 nucleotide sequence of VL Chain

<400> SEQUENCE: 16
ggtaaaaaca accggccctc a                                                    21

<210> SEQ ID NO 17
<211> LENGTH: 354
<212> TYPE: DNA
<213> ORGANISM: Artificial
<220> FEATURE:
<223> OTHER INFORMATION: VH Chain nucleotide sequence

<400> SEQUENCE: 17
atggccgagg tgcagctggt ggagtctggg ggaggcttgg tacggcctgg ggggtccctg           60
agactctcct gtgcagcctc tggattcacc tttagcagct atgccatgag ctgggtccgc          120
```

```
caggctccag ggaaggggct ggagtgggtc tcagctatta gtggtagtgg tggtagcaca      180
tactacgcag actccgtgaa ggccggttc  accatctcca gagacaattc aagaacacg       240 ctgtatctgc aaatgaacag cctgagagcc gaggacacgg ccgtatatta ctgtgcgaaa      300
tcgcataagc gttttgacta ctggggccag ggaaccctgg tcaccgtgtc gaga            354
```

<210> SEQ ID NO 18
<211> LENGTH: 327
<212> TYPE: DNA
<213> ORGANISM: Artificial
<220> FEATURE:
<223> OTHER INFORMATION: VL Chain nucleotide sequence

<400> SEQUENCE: 18

```
tcgtctgagc tgactcagga ccctgctgtg tctgtggcct gggacagac  agtcaggatc       60 acatgccaag agacagcct  cagaagctat tatgcaagct ggtaccagca gaagccagga      120
caggcccctg tacttgtcat ctatggtaaa acaaccggc  cctcagggat cccagaccga      180
ttctctggct ccagctcagg aaacacagct tccttgacca tcactggggc tcaggcggaa      240
gatgaggctg actattactg taactcctct tttccccgga cttcttctgt ggtattcggc      300
ggagggacca agctgaccgt cctaggc                                          327
```

<210> SEQ ID NO 19
<211> LENGTH: 42
<212> TYPE: DNA
<213> ORGANISM: Artificial
<220> FEATURE:
<223> OTHER INFORMATION: Linker nucleotide sequence

<400> SEQUENCE: 19

```
ggtggaggcg gttcaggcgg aggtggctct ggcggtggcg ga                          42
```

<210> SEQ ID NO 20
<211> LENGTH: 723
<212> TYPE: DNA
<213> ORGANISM: Artificial
<220> FEATURE:
<223> OTHER INFORMATION: scFv nucleotide sequence

<400> SEQUENCE: 20

```
atggccgagg tgcagctggt ggagtctggg ggaggcttgg tacggcctgg ggggtccctg       60
agactctcct gtgcagcctc tggattcacc tttagcagct atgccatgag ctgggtccgc      120
caggctccag ggaaggggct ggagtgggtc tcagctatta gtggtagtgg tggtagcaca      180
tactacgcag actccgtgaa ggccggttc  accatctcca gagacaattc aagaacacg       240 ctgtatctgc aaatgaacag cctgagagcc gaggacacgg ccgtatatta ctgtgcgaaa      300
tcgcataagc gttttgacta ctggggccag ggaaccctgg tcaccgtgtc gagaggtgga      360
ggcggttcag gcggaggtgg ctctggcggt ggcggatcgt ctgagctgac tcaggaccct      420
gctgtgtctg tggccttggg acagacagtc aggatcacat gccaaggaga cagcctcaga      480
agctattatg caagctggta ccagcagaag ccaggacagg cccctgtact tgtcatctat      540
ggtaaaaaca accggccctc agggatccca gaccgattct ctggctccag ctcaggaaac      600
acagcttcct tgaccatcac tggggctcag gcggaagatg aggctgacta ttactgtaac      660
tcctcttttc ccggacttc  ttctgtggta ttcggcggag ggaccaagct gaccgtccta      720
ggc                                                                    723
```

```
<210> SEQ ID NO 21
<211> LENGTH: 100
<212> TYPE: PRT
<213> ORGANISM: Artificial
<220> FEATURE:
<223> OTHER INFORMATION: Amino acid sequence of CD99 extracellular
      domain

<400> SEQUENCE: 21

Asp Gly Gly Phe Asp Leu Ser Asp Ala Leu Pro Asp Asn Glu Asn Lys
1               5                   10                  15

Lys Pro Thr Ala Ile Pro Lys Lys Pro Ser Ala Gly Asp Asp Phe Asp
            20                  25                  30

Leu Gly Asp Ala Val Val Asp Gly Glu Asn Asp Asp Pro Arg Pro Pro
        35                  40                  45

Asn Pro Pro Lys Pro Met Pro Asn Pro Asn Pro Asn His Pro Ser Ser
    50                  55                  60

Ser Gly Ser Phe Ser Asp Ala Asp Leu Ala Asp Gly Val Ser Gly Gly
65                  70                  75                  80

Glu Gly Lys Gly Gly Ser Asp Gly Gly Gly Ser His Arg Lys Glu Gly
                85                  90                  95

Glu Glu Ala Asp
            100

<210> SEQ ID NO 22
<211> LENGTH: 300
<212> TYPE: DNA
<213> ORGANISM: Artificial
<220> FEATURE:
<223> OTHER INFORMATION: Nucleotide sequence of CD99 extracellular
      domain

<400> SEQUENCE: 22
gatggtggtt tcgatttatc cgatgccctt cctgacaatg agaacaagaa acccactgca      60
atccccaaga aacccagtgc tggggatgac tttgacttag agatgctgt tgttgatgga     120 gaaaatgacg acccacgacc accgaaccca cccaaaccga tgccaaatcc aaaccccaac    180
caccctagtt cctccggtag cttttcagat gctgaccttg cggatggcgt ttcaggtgga    240
gaaggaaaag gaggcagtga tggtggaggc agccacagga agaagggga agaggccgac    300

<210> SEQ ID NO 23
<211> LENGTH: 28
<212> TYPE: DNA
<213> ORGANISM: Artificial
<220> FEATURE:
<223> OTHER INFORMATION: CD99 For Primer

<400> SEQUENCE: 23
cgatggatcc gatggtggtt tcgattta                                        28

<210> SEQ ID NO 24
<211> LENGTH: 21
<212> TYPE: DNA
<213> ORGANISM: Artificial
<220> FEATURE:
<223> OTHER INFORMATION: CD99 Rev Primer

<400> SEQUENCE: 24
acatgtcgac gtcggcctct t                                               21

<210> SEQ ID NO 25
<211> LENGTH: 25
<212> TYPE: PRT
```

-continued

```
<213> ORGANISM: Artificial
<220> FEATURE:
<223> OTHER INFORMATION: CD99 amino acid sequence representing the
      epitope

<400> SEQUENCE: 25

Gly Asp Asp Phe Asp Leu Gly Asp Ala Val Val Asp Gly Glu Asn Asp
1               5                   10                  15

Asp Pro Arg Pro Pro Asn Pro Pro Lys
            20                  25

<210> SEQ ID NO 26
<211> LENGTH: 17
<212> TYPE: DNA
<213> ORGANISM: Artificial
<220> FEATURE:
<223> OTHER INFORMATION: fdseq1 Primer

<400> SEQUENCE: 26
ggattttctg tatgagg                                                    17

<210> SEQ ID NO 27
<211> LENGTH: 20
<212> TYPE: DNA
<213> ORGANISM: Artificial
<220> FEATURE:
<223> OTHER INFORMATION: pelBback

<400> SEQUENCE: 27
agccgctgga ttgttattac                                                 20
```

SINGLE-CHAIN VARIABLE FRAGMENT (SCFV) ABLE TO RECOGNIZE AND BIND CD99 HUMAN PROTEIN

CROSS REFERENCE TO RELATED APPLICATIONS

The present application is the US national stage of International Application PCT/IB2010/055135 filed on Nov. 12, 2010 which, in turn, claims priority to Italian Patent Application MI2009A001994 filed on Nov. 13, 2009.

The present invention relates to a single-chain variable fragment (scFv) able to recognize and bind CD99 human protein.

Moreover, the present invention relates to the sequences, production and use, for diagnostic and pharmaceutical purposes, of said scFv.

In particular, said scFv is useful for the diagnosis and treatment of cancer, preferably the diagnosis and treatment of Ewing sarcoma.

CD99 is a transmembrane glycoprotein which, in humans, shows no homology to any other known proteins (except Xga). CD99 has a molecular mass of 32 kDa and is involved in important physiological functions, including cellular adhesion, apoptosis, T cell and thymocyte differentiation, monocyte migration and intracellular adhesion between lymphocytes and endothelial cells. In pathological conditions, and in particular in Ewing sarcoma cells, CD99 plays a key role in mediating apoptotic signals following adhesion between cells (4-5).

Ewing sarcoma is a tumour that can develop in any area of the body, though it originates most frequently from bones.

The rarity of these neoplasms and the complexity of therapy make treatment in highly specialised centres with multi-specialty competencies indispensable in order to ensure optimal patient therapy and rehabilitation, as well as improve their survival and quality of life.

The new therapeutic approaches to Ewing sarcoma have brought the percentages of patient survival to 70%. Said approaches involve, first of all, a precise, accurate diagnosis, followed by targeted surgical interventions combined with radiological and chemotherapy treatments. However, the recent therapeutic innovations have not significantly influenced the outcomes of treatments for patients affected with metastatic or recurrent Ewing sarcoma; in fact, the survival rate in these cases is less than 25%. The extremely unfavourable outcome percentages associated with treatment of this sarcoma have remained practically unchanged in the past decades and have not significantly improved despite the efforts made by researchers worldwide to introduce new chemotherapy models which include antitumour drugs with different mechanisms of action (1).

The sensitivity to radiotherapy treatment makes local control of Ewing sarcoma possible by relying on surgery, radiotherapy or both, depending on the clinical situation. The current trend, however, favours the surgical approach, which in nearly all cases consists in a conservative treatment that restricts the use of radiotherapy to situations where surgical intervention would not be able to guarantee an oncologically adequate resection.

Non-randomized clinical studies clearly demonstrate that chemotherapy treatment associated with surgery and/or radiotherapy offers a significant advantage over surgical and/or radiotherapy treatment alone.

The chemotherapy drugs most widely used in the treatment of Ewing sarcoma include adriamycin, ifosfamide, cyclophosphamide, etoposide, vincristine and dactinomycin.

However, said tumour is characterized by a natural and/or acquired multiple resistance to the drugs used in conventional chemotherapy.

For some time, therefore, a strong need has been felt to identify new molecules to be used, either individually or in combination with classic chemotherapy treatments, and/or to be associated with alternative therapeutic treatments (surgical resection/radiotherapy), for the treatment of Ewing sarcoma.

In general, these skeletal muscle sarcomas represent a group of relatively rare tumours for which there exists a great demand for new treatment schemes that combine a higher probability of recovery and fewer long-term toxic side effects compared to the antitumour therapies currently used. In order to achieve this aim, a number of innovative therapeutic approaches can be taken into consideration, including the use of monoclonal antibodies, which in the past few years have been taking on a leading role in the treatment of solid tumours, previously considered untreatable. This is due to a series of factors which include the high effectiveness and good tolerability of immunotherapy compared to conventional antitumour treatments. Furthermore, it is evident from data reported in the literature and deriving from numerous clinical trials that a good response to immunotherapy treatment in patients affected by solid metastatic tumours becomes an excellent one when combined with chemotherapy.

In light of these observations, and considering the extremely aggressive nature of skeletal muscle sarcomas, it is evident that a favourable immunotherapy, also in combination with the administration of chemotherapy drugs, could represent an effective, sufficiently safe (2-3) treatment strategy for this type of pathology.

As noted above, monoclonal antibodies have recently received particular clinical attention.

An antibody, or more strictly speaking an immunoglobulin, is a protein with a peculiar "Y"-shaped modular quaternary structure; an antibody is capable of binding to complementary structures called antigens in a highly specific manner.

In an antibody two fundamental components can be distinguished (see FIG. 1):
  a constant region (C), which mediates the interaction of the antibody with the complement or cells of innate immunity ("Fc" portion).
  a variable region (V), which contains the site of combination with the antigen and is thus variable according to the specificity of the antibody for a given antigen ("Fab" portion).

Said components are structured so as to form a tetrameric complex composed of four chains of glycoproteins, two heavy chains (H), which are equal to each other, and two light chains (L), likewise equal to each other.

Each chain moreover consists of a variable domain (VH for the heavy chain, VL for the light chain) placed at the amino-terminal end and one or more constant domains at the carboxy-terminal end (see FIG. 1). Finally, in each variable domain, at the antigen-binding site, there are present 3 hypervariable regions (CDR1, CDR2 and, lastly, the most variable portion, CDR3) with so-called framework regions set between them. At the structural level, the hypervariable regions are organised so as to form three closely spaced loops within a complex structure of beta sheets derived from the framework regions.

Human immunoglobulins are divided into 5 main classes: IgG, IgA, IgM, IgD, IgE.

Antibodies can be obtained by relying on a number of procedures, which include:

chimerization/humanization of murine antibodies (4), use of transgenic mice together with the conventional system of hybridomas and immortalization of human B lymphocytes by transformation with EBV (5, 6).

The antibodies can be fragmented in order to eliminate the Fc portion and ensure a lower immunogenicity. The antibody fragments that are obtained and to which reference will be made hereinafter in this patent application when use is made of the term "antibody fragments", are F(ab')$_2$, Fab' and scFv (see FIG. 1).

A particular type of antibody fragment is defined as scFv, an acronym of "single-chain variable fragment".

This molecule is a fusion of the variable regions of the light chain (VL) and of the heavy chain (VH) of the immunoglobulins, held together by a linker (see FIG. 1). The linker can be a flexible peptide which enables the VH-VL chains to take on the correct structure as a functional monomeric unit. This chimeric molecule maintains the specificity of the original immunoglobulin and can be engineered to form "diabodies" or bivalent scFv (see FIG. 1), by joining together two scFv. Unlike the monoclonal antibodies often produced in mammalian cell cultures, the scFv fragments are very often produced through bacterial cell cultures, such as of *Escherichia coli*.

Murine anti-CD99 monoclonal antibodies, obtained by means of hybridoma technology, have been tested in animal models for their ability to significantly reduce Ewing sarcoma tumour masses (2). However, murine monoclonal antibodies cannot be used in a clinical setting due to their xenogenic origin, which could give rise to dangerous adverse effects in patients (3).

Furthermore, even if a certain number of murine monoclonal antibodies directed against the extracellular domain of CD99 have been previously isolated and described, both with respect to immunochemical characteristics and specificity (12), their use is impossible according to the objects of the present invention since they recognize epitopes of CD99 which are expressed on a large part of normal and transformed tissues and, consequently, they do not represent reagents able to discriminate any isoforms or epitopes selectively expressed on cells of Ewing sarcoma.

To date there are no known antibody fragments, in particular scFv, directed against CD99.

The technical problem illustrated above finds a solution in the present invention, relating to a single-chain variable fragment (scFv) able to recognize and bind CD99 human protein in a specific and selective manner.

Furthermore, the present invention relates to the sequences and production of said scFv.

Finally, the invention relates to the use of said scFv for diagnostic and pharmaceutical purposes, in particular for the treatment of cancer, preferably Ewing sarcoma.

Unlike other anti-CD99 monoclonal antibodies described in the prior art, an scFv, according to the present invention, was produced for the first time using the technique of unfolding proteins on phages and provides the following advantages:

i) it is completely human;
ii) it is administered without the complications arising from immune responses against xenogenic antigens;
iii) it is formed by a heavy variable chain (VH) and a light variable chain (VL) of human immunoglobulins held together by a linker (see diagram in FIG. 4 and FIG. 1). The molecule possesses a molecular mass of 27-30 kDa in place of the 145-150 kDa characteristic of antibodies in IgG form;
iv) it is produced without having recourse to animal immunization;
v) it is produced by bacterial fermentation and, consequently, can be easily and quickly obtained in large quantities;
vi) it is free of human pathogens;
vii) it reacts, in a selective and specific manner, with an epitope of the extracellular fraction of CD99, which is expressed or is made accessible by the structural and molecular characteristics of the antibody fragment according to the present invention only on Ewing sarcoma cells. The same epitope of CD99 is not present on other either normal or transformed cell types, including osteosarcoma cells.

The scFv antibody fragment, according to the present invention, possesses all of the characteristics necessary in a biological compound for use in the diagnosis and treatment of Ewing sarcoma.

Said characteristics regard the fact that it is human, and thus has low or no immunogenicity; moreover, it interacts in a specific and selective manner with an epitope included in the CD99 determinant expressed on Ewing sarcoma cells. Finally, the reduced molecular size of the antibody fragment according to the present invention enables a homogeneous diffusion and penetration into tumour tissues as well as fast blood elimination.

On the basis of these characteristics, the scFv antibody fragment to which the present invention relates is unlike any other anti-CD99 antibody or fragment thereof disclosed in the prior art.

BRIEF DESCRIPTION OF DRAWINGS

The invention is described hereinafter with particular reference to the appended figures in which.

DETAILED DESCRIPTION

The invention to which the present patent application relates concerns a single-chain variable fragment (scFv) able to recognize and bind CD99 human protein.

Furthermore, the present invention relates to the sequences, production and use, for diagnostic and pharmaceutical purposes, of said scFv. In particular, said scFv is useful for the treatment of cancer, preferably Ewing sarcoma.

Figure 1:
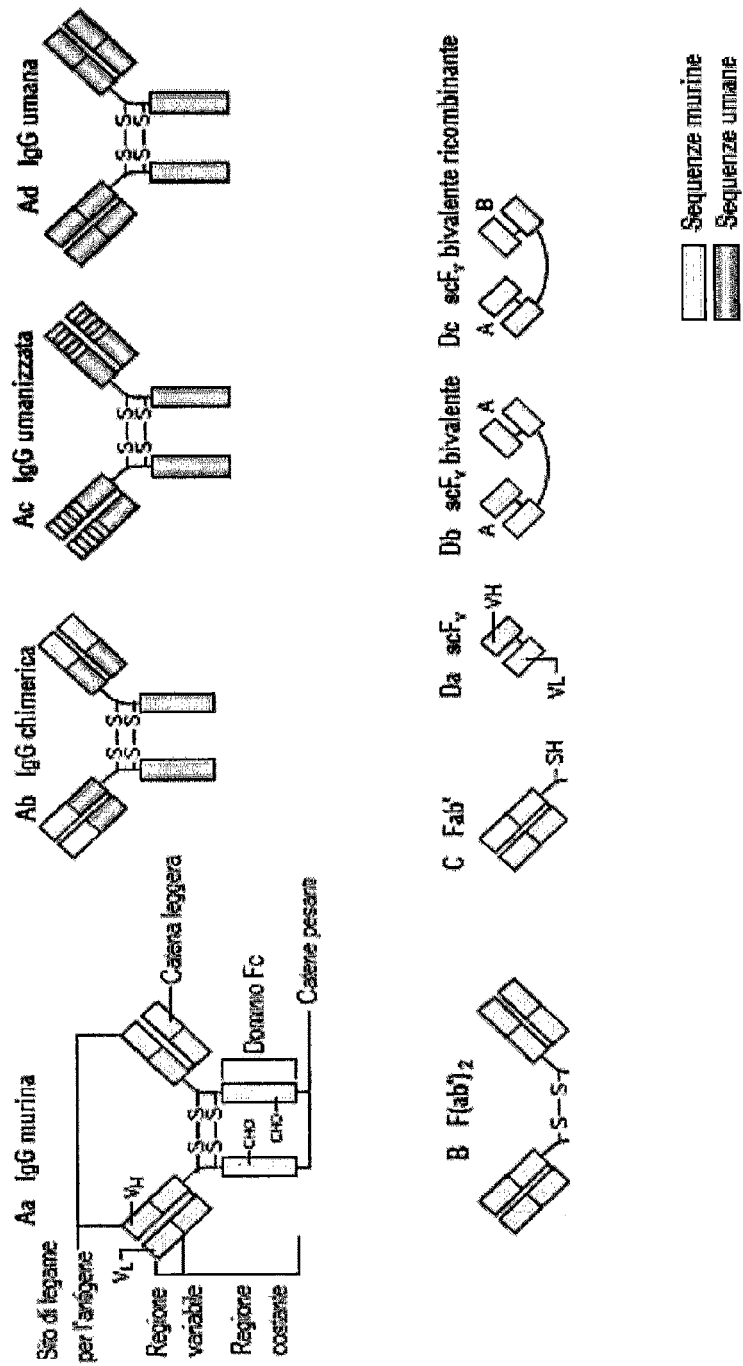
FIG. 1 shows the schematized structure of antibodies and antibody fragments: the antibodies used most widely in clinical practice and in research are usually G immunoglobulins (IgG) (Aa) or fragments of immunoglobulins (B-D); the F(ab')$_2$ (B) or Fab' (C) fragments can be obtained by enzymatic splitting on the entire antibody;
VH: variable region of the heavy chain;
VL: variable region of the light chain.

The single-chain variable fragment (scFv) to which the invention relates preferably consists of a variable portion of the light chain (VL) and a variable portion of the heavy chain (VH) of an immunoglobulin, held together by a linker (see FIG. 1).

In each variable domain, at the antigen-binding site, there are present 3 hypervariable regions (CDR1, CDR2 and, lastly, the most variable portion, CDR3) with so-called framework regions set between them.

Said scFv can be engineered to form "diabodies" or bivalent scFv formed by two scFv molecules.

The linker can be a flexible peptide that enables the VH-VL chains to take on the correct structure, i.e. that of a functional monomeric unit.

In one embodiment of the present invention, the scFv comprises a VH chain and a VL chain held together by a linker.

Each VH and VL chain comprises at least one hypervariable region, preferably the CDR3 region.

Preferably, each VH and VL chain also comprises the two further variable regions CDR1 and CDR2.

In a preferred embodiment, each VH and VL chain comprises 3 hypervariable regions defined as CDR1, CDR2 and CDR3 (CDR3 represents the most highly variable region). CDR1, CDR2 and CDR3 are responsible for antigen recognition and have so-called framework regions set between.

Preferably, the CDR3 amino acid sequence of the VH chain is defined by SEQ ID NO: 1. Said sequence is shown in table 1. In the sequence in table 1 the amino acids susceptible to the greatest variability are underlined.

Preferably, the CDR3 amino acid sequence of the VL chain is defined by SEQ ID NO: 2. Said sequence is shown in table 1. In the sequence in table 1 the amino acids susceptible to the greatest variability are underlined.

Therefore, the invention comprises all of the functional variants of scFv which are characterized by identical CDR3 regions.

Preferably, the CDR1 and CDR2 amino acid sequences of the VH chain are defined by SEQ ID NO: 3 and 4.

Preferably, the CDR1 and CDR2 amino acid sequences of the VL are defined by SEQ ID NO: 5 and 6.

Therefore, the invention comprises all of the functional variants of scFv which are characterized by identical CDR regions.

More preferably, the amino acid sequence of the VH chain is defined by SEQ ID NO: 7.

More preferably, the amino acid sequence of the VL chain is defined by SEQ ID NO: 8.

The amino acid sequence of the linker that joins VH and VL is preferably defined by SEQ ID NO: 9.

The preferred embodiment of the present invention relates to the scFv fragment whose amino acid sequence essentially consists of SEQ ID NO: 10.

The present invention also relates to all amino acid sequences characterized by at least 95% identity with the amino acid sequences described in the present patent application.

A further aspect of the invention concerns the nucleotide sequences of the scFv molecule which encode the above-described amino acid sequences of the scFv fragment.

In one embodiment of the present invention, the CDR3 nucleotide sequence of the VH chain is defined by SEQ ID NO: 11, while the CDR3 nucleotide sequence of the VL chain is defined by SEQ ID NO: 12. Table 1 shows the sequences 11 and 12, in which the nucleotide residues susceptible to the greatest variability are underlined.

Preferably, the CDR1 and CDR2 nucleotide sequences of the VH chain are defined by SEQ ID NO: 13 and 14, while the CDR1 and CDR2 nucleotide sequences of the VL chain are defined by SEQ ID NO: 15 and 16.

More preferably, the nucleotide sequence of the VH chain is defined by SEQ ID NO: 17, whereas the nucleotide sequence of the VL chain is defined by SEQ ID NO: 18.

The nucleotide sequence of the linker which joins VH and VL is preferably defined by SEQ ID NO: 19.

The preferred embodiment of the present invention relates to the scFv fragment whose nucleotide sequence essentially consists of SEQ ID NO: 20.

The subject matter of the invention also includes all of the nucleotide sequences derived from the nucleotide sequences shown in table 1, for example as a result of degeneration of the genetic code.

A further aspect of the invention also relates to immunoglobulins, preferably monoclonal antibodies, which comprise at least one of the amino acid sequences defining an scFv according to the invention.

Said immunoglobulins can be obtained with methods which include, for example, hybridoma technology capable of producing human, humanized or chimeric immunoglobulins derived from the sequences characterizing an scFv according to the invention.

Yet a further aspect of the invention relates to antibody fragments obtained using recombinant DNA procedures on the basis of the sequences characterizing an scFv according to the invention.

The sequences of the invention are presented according to the international standard WIPO ST.25 and the description thereof was developed with the program Pantent-In 3.3.

A description of the sequences is appended hereto.

Table 1 below shows all of the amino acid and nucleotide sequences and the corresponding "Sequence Identifiers", which define the scFv molecule as described in the present invention.

TABLE 1

| SEQ ID NO: 1 | 99-A K <u>S H K R</u> F D Y-107 | CDR3 amino acid sequence of the VH chain |
|---|---|---|
| SEQ ID NO: 2 | 220-N S S <u>F P R T S S</u> V V-230 | CDR3 amino acid sequence of the |

TABLE 1-continued

| SEQ ID NO: 3 | 28-G F T F S S Y A M S-37 | CDR1 amino acid sequence of the VH chain |
|---|---|---|
| SEQ ID NO: 4 | 52-A I S G S G G S T-60 | CDR2 amino acid sequence of the VH chain |
| SEQ ID NO: 5 | 155-Q G D S L R S Y Y A S-165 | CDR1 amino acid sequence of the VL chain |
| SEQ ID NO: 6 | 181-G K N N R P S-187 | CDR2 amino acid sequence of the VL chain |
| SEQ ID NO: 7 | 1 - M A E V Q L V E S G G G L V R P G G S   L R L S C A A S G F T F S S Y A M S W V R   Q A P G K G L E W V S A I S G S G G S T Y   Y A D S V K G R F T I S R D N S K N T L Y   L Q M N S L R A E D T A V Y Y C A K S H K   R F D Y W G Q G T L V T V S R-118 | Amino acid sequence of the VH chain |
| SEQ ID NO: 8 | 133-S S E L T Q D P A V S V A L G Q T V R I T C Q G D S L R S Y Y A S W Y Q Q K P G Q A P V L V I Y G K N N R P S G I P D R F   S G S S S G N T A S L T I T G A Q A E D E   A D Y Y C N S S F P R T S S V V F G G G T K L T V L G-241 | Amino acid sequence of the VL chain |
| SEQ ID NO: 9 | 119-G G G G S G G G G S G G G G-132 | Amino acid sequence of the linker |
| SEQ ID NO: 10 | 1-M A E V Q L V E S G G G L V R P G G S L R L S C A A S G F T F S S Y A M S W V R Q A P G K G L E W V S A I S G S G G S T Y Y A D S V K G R F T I S R D N S K N T L Y L Q M N S L R A E D T A V Y Y C A K S H K R F D Y W G Q G T L V T V S R G G G G S G G G G S G G G G S S E L T Q D P A V S V A L G Q T V R I T C Q G D S L R S Y Y A S W Y Q Q K P G Q A P V L V I Y G K N N R P S G I P D R F S G S S S G N T A S L T I T G A Q A E D E A D Y Y C N S S F P R T S S V V F G G G T K L T V L G-241 | Amino acid sequenze of scFv fragment |
| SEQ ID NO: 11 | 295-GCG AAA TCG CAT AAG CGT TTT GAC TAC-321 | CDR3 nucleotide sequence of the VH chain |
| SEQ ID NO: 12 | 658-AAC TCC TCT TTT CCC CGG ACT TCT TCT GTG GTA-690 | CDR3 nucleotide sequence of the VL chain |
| SEQ ID NO: 13 | 82-GGA TTC ACC TTT AGC AGC TAT GCC ATG AGC-111 | CDR1 nucleotide sequence of the VH chain |
| SEQ ID NO: 14 | 154-GCT ATT AGT GGT AGT GGT GGT AGC ACA-180 | CDR2 nucleotide sequence of the VH chain |
| SEQ ID NO: 15 | 463-TGC CAA GGA GAC AGC CTC AGA AGC TAT TAT GCA AGC-495 | CDR1 nucleotide sequence of the VL chain |
| SEQ ID NO: 16 | 541-GGT AAA AAC AAC CGG CCC TCA-561 | CDR2 nucleotide sequences of the VL chain |
| SEQ ID NO: 17 | 1-ATG GCC GAG gTG CAG CTG GTG GAG TCT GGG GGA GGC TTG GTA CGG CCT GGG | Nucleotide sequence of the |

TABLE 1-continued

| | | |
|---|---|---|
| | GGG TCC CTG AGA CTC TCC TGT GCA GCC<br>TCT GGA TTC ACC TTT AGC AGC TAT GCC<br>ATG AGC TGG GTC CGC CAG GCT CCA GGG<br>AAG GGG CTG GAG TGG GTC TCA GCT ATT<br>AGT GGT AGT GGT GGT AGC ACA TAC TAC<br>GCA GAC TCC GTG AAG GGC CGG TTC ACC<br>ATC TCC AGA GAC AAT TCC AAG AAC ACG<br>CTG TAT CTG CAA ATG AAC AGC CTG AGA<br>GCC GAG GAC ACG GCC GTA TAT TAC TGT<br>GCG AAA TCG CAT AAG CGT TTT GAC TAC<br>TGG GGC CAG GGA ACC CTG GTC ACC GTG<br>TCG AGA-354 | VH chain |
| SEQ ID NO:<br>18 | 397-TCG TCT GAG CTG ACT CAG GAC CCT<br>GCT GTG TCT GTG GCC TTG GGA CAG ACA<br>GTC AGG ATC ACA TGC CAA GGA GAC AGC<br>CTC AGA AGC TAT TAT GCA AGC TGG TAC<br>CAG CAG AAG CCA GGA CAG GCC CCT GTA<br>CTT GTC ATC TAT GGT AAA AAC AAC CGG<br>CCC TCA GGG ATC CCA GAC CGA TTC TCT<br>GGC TCC AGC TCA GGA AAC ACA GCT TCC<br>TTG ACC ATC ACT GGG GCT CAG GCG AAA<br>GAT GAG GCT GAC TAT TAC TGT AAC TCC<br>TCT TTT CCC CGG ACT TCT TCT GTG GTA<br>TTC GGC GGA GGG ACC AAG CTG ACC GTC<br>CTA GGC 723 | Nucleotide<br>sequence of the<br>VL chain |
| SEQ ID NO:<br>19 | 355-GGT GGA GGC GGT TCA GGC GGA GGT<br>GGC TCT GGC GGT GGC GGA-396 | Nucleotide<br>sequence of the<br>linker |
| SEQ ID NO:<br>20 | 1-ATG GCC GAG GTG CAG CTG GTG GAG<br>TCT GGG GGA GGC TTG GTA CGG CCT GGG<br>GGG TCC CTG AGA CTC TCC TGT GCA GCC<br>TCT GGA TTC ACC TTT AGC AGC TAT GCC<br>ATG AGC TGG GTC CGC CAG GCT CCA GGG<br>AAG GGG CTG GAG TGG GTC TCA GCT ATT<br>AGT GGT AGT GGT GGT AGC ACA TAC TAC<br>GCA GAC TCC GTG AAG GGC CGG TTC ACC<br>ATC TCC AGA GAC AAT TCC AAG AAC ACG<br>CTG TAT CTG CAA ATG AAC AGC CTG AGA<br>GCC GAG GAC ACG GCC GTA TAT TAC TGT<br>GCG AAA TCG CAT AAG CGT TTT GAC TAC<br>TGG GGC CAG GGA ACC CTG GTC ACC GTG<br>TCG AGA GGT GGA GGC GGT TCA GGC GGA<br>GGT GGC TCT GGC GGT GGC GGA TCG TCT<br>GAG CTG ACT CAG GAC CCT GCT GTG TCT<br>GTG GGA CAG ACA GTC AGG ATC ACA TGC<br>CAA GGA GAC AGC CTC AGA AGC TAT TAT<br>GCA AGC TGG TAC CAG CAG AAG CCA GGA<br>CAG GCC CCT GTA CTT GTC ATC TAT GGT<br>AAA AAC AAC CGG CCC TCA GGG ATC CCA<br>GAC CGA TTC TCT GGC TCC AGC TCA GGA<br>AAC ACA GCT TCC TTG ACC ATC ACT GGG<br>GCT CAG GCG AAA GAT GAG GCT GAC TAT<br>TAC TGT AAC TCC TCT TTT CCC CGG ACT<br>TCT TCT GTG GTA TTC GGC GGA GGG ACC<br>AAG CTG ACC GTC CTA GGC-723 | Nucleotide<br>sequence of scFv<br>fragment |
| SEQ ID NO:<br>21 | 23-D G G F D L S D A L P D N E N K<br>K P T A I P K K P S A G D D F D L<br>G D A V V D G E N D D P R P P N P<br>P K P M P N P N P N H P S S S G S<br>F S D A D L A D G V S G G E G K G<br>G S D G G S H R K E G E E A D-122 | Amino acid<br>sequence of the<br>extracellular<br>domain of CD99 |
| SEQ ID NO:<br>22 | 67- GAT GGT GGT TTC GAT TTA TCC GAT<br>GCC CTT CCT GAC AAT GAG AAC AAG AAA<br>CCC ACT GCA ATC CCC AAG AAA CCC AGT<br>GCT GGG GAT GAC TTT GAC TTA GGA GAT<br>GCT GTT GTT GAT GGA GAA AAT GAC GAC<br>CCA CGA CCA CCG AAC CCA CCC AAA CCG<br>ATG CCA AAT CCA AAC CCC AAC CAC CCT<br>AGT CCT CCG GTA GCT TTT TCA GAT GCT<br>GAC CTT GCG GAT GGC GTT TCA GGT GGA<br>GAA GGA AAA GGA GGC AGT GAT GGT GGA<br>GGC AGC CAC AGG AAA GAA GGG GAA GAG<br>GCC GAC -366 | Gene encoding<br>the<br>extracellular<br>domain of D99 |

TABLE 1-continued

| SEQ ID NO: 23 | 5'CGATGGATCCGATGGTGGTTTCGATTTA-3' | Primer CD99For |
| --- | --- | --- |
| SEQ ID NO: 24 | 5'-ACATGTCGACGTCGGCCTCTT-3' | Primer CD99Rev |
| SEQ ID NO: 25 | 50- G D D F D L G D A V V D G E N D D P R P P N P P K -74 | Epitope: amino acids 50-74 of the extracellular domain of CD99 |
| SEQ ID NO: 26 | 5'-GGATTTTCTGTATGAGG-3' | Primer fdseq1 |
| SEQ ID NO: 27 | 5'-AGCCGCTGGATTGTTATTAC-3' | Primer pelBback |

The invention further relates to an expression vector comprising the nucleotide sequences as described. Said expression vector comprises nucleotide sequences necessary for the expression, in a host cell, of the scFv-encoding sequences according to the invention.

The sequences necessary for expression in prokaryotes regard a promotor and, optionally, an operator sequence, a ribosome binding site and possibly other sequences.

For expression in eukaryotic cells, on the other hand, sequences such as promotors, enhancers, termination signals and polyadenylation are required.

Said expression vector can also contain a signal sequence for directing the expression of an scFv in a particular cellular compartment, e.g. to the membrane, or for the secretion of an scFv, or for directing the expression of an scFv on the periplasm of a bacterium.

Preferably bacterial periplasmic expression can be achieved using as vehicles signal sequences such as ompA, ompF, ompT, LamB, b-lactamase, cp VIII of M13, malE, phoA, and preferably the sequence pelB.

Said vector can also contain, under the same promotor, a selection gene whose expression can be easily used to select the recombinant host cells, which are thus transformed with the expression vector containing them. Classic selection genes are those which impart resistance to antibiotics, fluorescent genes, or other genes easily monitorable by a person skilled in the art.

The invention also relates to a host cell comprising an expression vector as described above.

Said host cells can be prokaryotic or eukaryotic and can be obtained by transformation or transfection of the host cells with the expression vectors according to the present invention.

Gram-positive and gram-negative bacteria are included among the prokaryotic cells. Among the gram-negative bacteria, *Escherichia coli* is preferred.

According to a preferred embodiment of the present invention, said scFv is directed against the extracellular domain of CD99, preferably the amino acid sequence SEQ ID NO: 21. Preferably, said scFv is able to recognize and bind an epitope located within the sequence limited by the amino acids 50-74 (SEQ ID NO: 25) of the extracellular fraction of CD99.

In a further embodiment of invention, said scFv is able to recognize and interact with the extracellular domain of CD99, preferably with an epitope located within the sequence limited by the amino acids 50-74 (SEQ ID NO: 25) of the extracellular fraction of CD99, selectively expressed by Ewing sarcoma cells and not by other tumour cells, including osteosarcomas (see experimental results in table 2).

In a further aspect of the invention, said scFv is used for diagnostic purposes, to detect and distinguish the Ewing sarcoma cells from those of other types of tumours, including osteosarcomas. More preferably, the typing of Ewing sarcoma cells is achieved by cytofluorometric, immunohistochemical or immunofluorescence studies.

In a further aspect of the invention, said scFv is used for therapeutic purposes for the treatment of cancer, alone or in combination with other conventional therapeutic treatments.

Said scFv can also be administered in combination with other chemotherapy agents or can stand alongside alternative therapeutic treatments, such as surgical resection and/or radiotherapy.

More preferably the cancer can be Ewing sarcoma.

The combination with other chemotherapy agents may involve the following drugs: adriamycin, ifosfamide, cyclophosphamide, etoposide, vincristine and dactinomycin and the administration thereof can accompany alternative antitumor therapeutic treatments, such as surgical resection and/or radiotherapy.

According to a specific embodiment of the present invention, said scFv can be used for therapeutic or diagnostic purposes, in particular for delivery into tumour cells, preferably Ewing sarcoma cells, of cytotoxic compounds, preferably with antitumour action, including anthracycline, calicheamicin, maytansine (macrolides) and auristatine; radionuclides chosen from the group comprising Iodine-124, Iodine-131, Copper-64 and Yttrium-90; biological products, e.g. enzymes such as cytosine deaminase, derived from bacteria or yeast, for the conversion of prodrugs into powerful antitumour compounds; lymphokines and chemokines which include IL-2, TNF alpha and IFN-gamma.

The invention also relates to an immunodiagnostic kit for the recognition of CD99 human protein, in particular the extracellular domain of CD99, preferably the epitope 50-74.

The immunodiagnostic kit is used for tumour diagnosis, in particular to diagnose Ewing sarcoma.

The kit comprises a single-chain variable fragment (scFv) and/or antibody and/or antibody fragment chosen from the group consisting of Fab', Fab", VH, VHH, VL and VLL together with single-use sterile materials for carrying out the diagnostic procedure.

According to a preferred embodiment of the present invention, said scFv was obtained using the method known as unfolding of immunoglobulin fragments on phages.

Said method consists in selecting human antibodies in the form of a single-chain variable fragment (scFv), by incubation, cyclically repeated, of a phage antibody display library on an antigen.

The scFv antibody fragment identified with the above-described method is amplified through a process of bacterial fermentation comprising the following steps:

a) infecting host cells, for example *E. coli* cells, with a phage in a culture medium;
b) inducing expression of the antibody and amplifying the host cell;
c) purifying the scFv molecule;
d) optionally concentrating by precipitation and dyalizing the scFv molecule.

In step c), if the scFv molecule is soluble, after purification it is necessary to recover the cell supernatant.

In addition, the scFv molecule can be tagged, for example with a histidine tail, for the purpose of purifying it by affinity chromatography.

Experimental Part

For the purpose of isolating human scFv specific for the extracellular domain of CD99, an aliquot of the ETH2 human synthetic phage antibody library, containing approximately $10^{12}$ phages cfu, was used for panning on the antigen CD99/GST (see paragraph "antigens and proteins") by means of a competitive selection strategy, in order to increase the possibility of identifying phage antibodies of the desired specificity (14, 15, 16).

The ETH2 phage antibody library was first incubated in an immunotube coated with GST and the unbound phages were used for panning on CD99/GST. After incubation with the CD99/GST-coated immunotube, the phages were removed with numerous washes and the phages specific for CD99/GST were eluted, amplified and used for a subsequent panning cycle (13).

Figure 2:
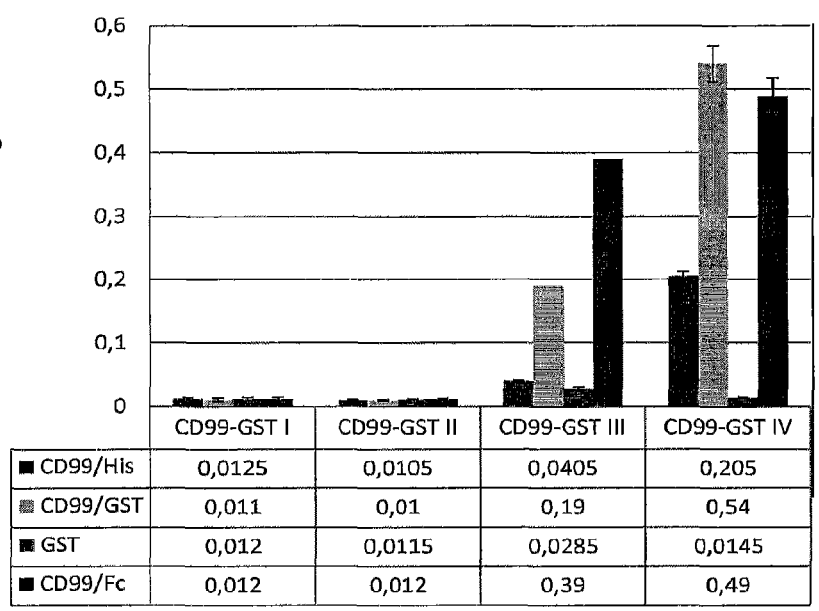
FIG. 2 shows the isolation of phage scFv from the ETH-2 antibody library selected on recombinant GST-conjugated CD99 (RCD99/GST) and ELISA assays of phage scFv populations on rCD99/GST; part A shows the progressive increase in the phage titre corresponding to the scFv population recovered after each single selection cycle; part B shows the ELISA-measured reactivity of the phage scFv population after each single selection cycle.

This selection strategy was repeated four times (see FIG. 2).

The polyclonal phage population, eluted after each individual panning cycle and characterized by a progressive increase in the phage titre of recovery (see FIG. 2A), was examined by ELISA.

Using this protocol it was possible to isolate a phage antibody population specific for CD99 after the fourth panning cycle, considering that no cross-reactivity with GST was observed.

Agar plating of bacteria infected with an aliquot of phage antibodies originating from the fourth selection enabled growth of the individual clones that host the phagemid, which were analyzed by ELISA on recombinant CD99/GST protein.

Surprisingly, one of these clones called scFvC7, is the most reactive in ELISA and recognizes and binds CD99 in a selective and specific way. In particular, scFvC7 is able to recognize and interact with an epitope located within the sequence limited by the amino acids 50-74 (SEQ ID NO: 25) of the extracellular fraction of CD99 expressed on Ewing sarcoma cells and shows no cross-reactivity with CD99 present on other cell types.

The C7 clone was amplified and the soluble scFv protein produced was analyzed for the recognition of recombinant CD99 of varying origin (see paragraph "Antigens and proteins").

Figure 3:
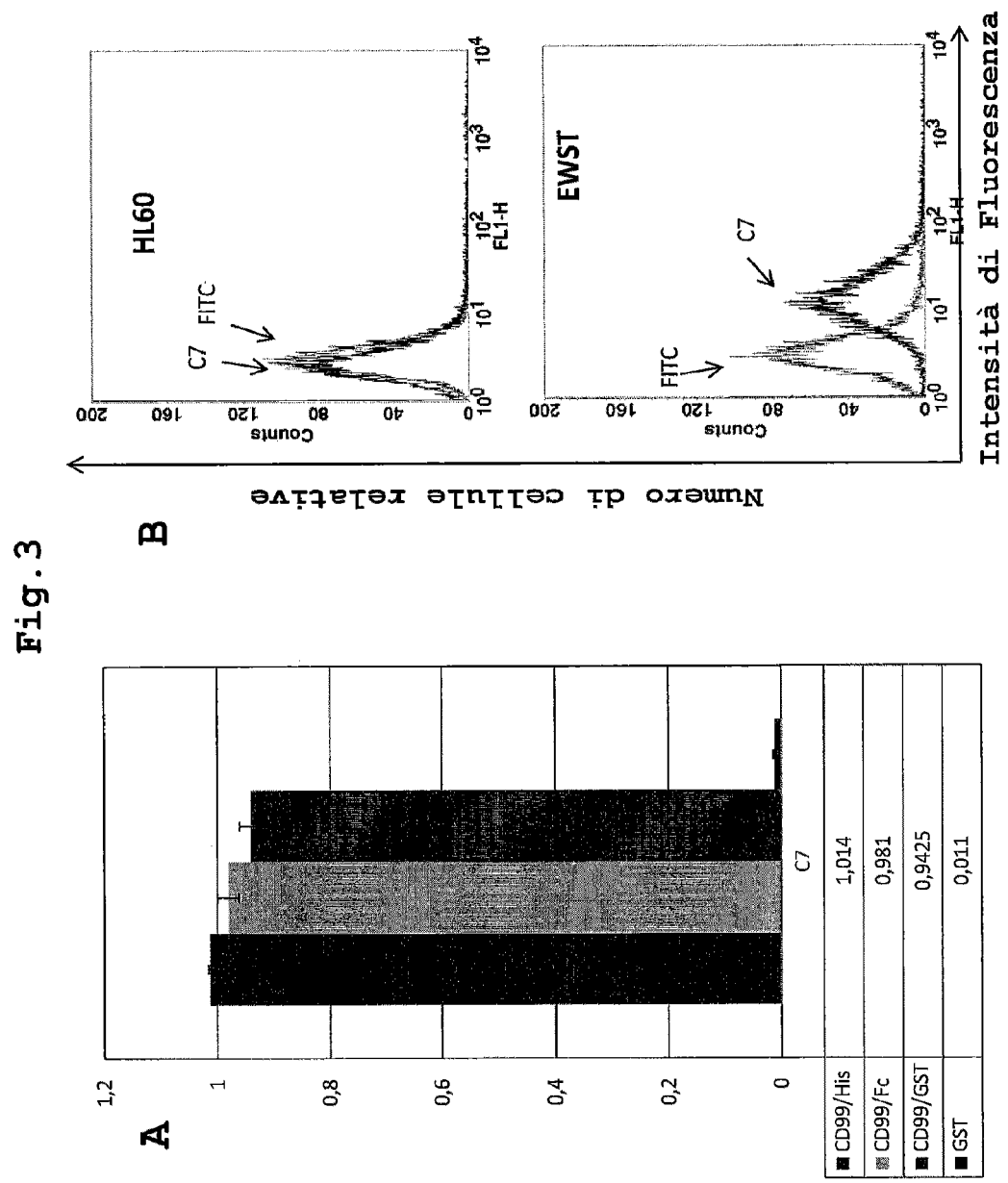
FIG. 3 shows the specificity of scFvC7 derived from cloning of the phage scFv population recovered after the 4th selection cycle; part A shows the ELISA reactivity of the clone scFvC7 tested against recombinant CD99 of varying origin and production; part B shows the cytofluorometric measurement of scFvC7 on lymphoid cells (HL60) expressing CD99, but not recognized by scFvC7, and on cells representing Ewing sarcoma (TC71), selectively recognized by scFvC7.

The results of this study are given in FIG. 2 and show that the C7 clone recognizes CD99/Fc and CD99/His, whereas no reactivity with GST or other control proteins was observed. The scFvC7 antibody clone recognizes cell lines of Ewing sarcoma (see Table 2) and reacts with human CD99 of varying origin (see FIG. 3) indicating that this antibody, called scFvC7, represents an excellent, sensitive molecule, useful for the diagnosis and treatment of Ewing sarcoma.

Figure 4:
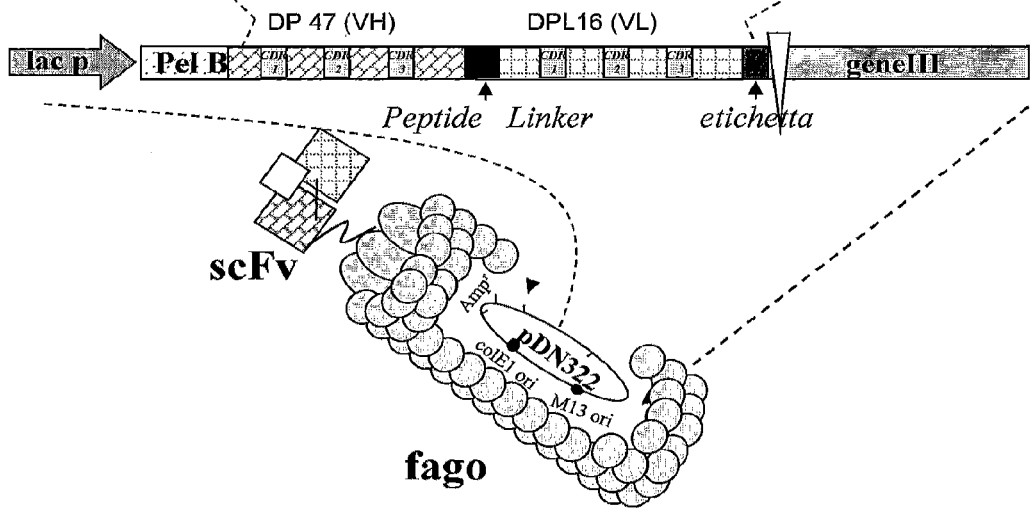
FIG. 4 shows the DNA sequence that encodes scFvC7 (SEQ ID NO 20) and the related amino acidic sequence (SEQ ID NO 10); the figure shows both the amino acid sequence in a three-letter code (SEQ ID NO: 7 and SEQ ID NO: 8) and the nucleotide sequence (SEQ ID NO: 17 and SEQ ID NO: 18) of the VH and VL immunoglobulin chains; the VH sequences are also italicized (SEQ ID NO: 7 and SEQ ID NO: 17); the sequence of the peptide that whereas the CDR3 joins the VH and VL region of the VH is underlined (SEQ ID NO: 9 and SEQ ID NO: 19), and VL is in boldface; the lower part of the figure shows a simplified diagram of the scFv antibody fragment unfolded on phage M13 as a fusion protein.

The genetic-molecular analyses show that the VH and VL sequences are correctly expressed and that the CDR3 regions are genetically distinct from all the scFv antibodies isolated to date from the ETH2 library (see FIG. 4).

The cytofluorometric studies conducted on live/intact cells which express the CD99 determinant show that scFvC7 recognizes solely the original Ewing sarcoma cells and not the other cell types that express CD99 (see Table 2).

TABLE 2

Specific and selective recognition of scFvC7 antibody towards Ewing sarcoma tumour cells as determined by cytofluorometric study

| Cells | Antibodies | | | | |
|---|---|---|---|---|---|
| | mAbO13 | scFvC7 | mAb0662 | scFvGO | mAbIgG |
| Ewing sarcoma | | | | | |
| TC-71 | ++ | +/− | +++ | − | − |
| LAP-35 | +++ | + | ND | − | − |
| 6647 | +++ | +++ | +++ | − | − |
| RD-ES | ++ | ++ | ND | − | − |
| SKES-1 | ++ | − | ND | − | − |
| IOR/RCH | +++ | ++ | ND | − | − |
| IOR/NGR | +++ | +/− | ND | − | − |
| IOR/BRZ | +++ | ++ | ND | − | − |
| WE-68 | +++ | +++ | ND | − | − |
| H-825 | ++ | ++ | ND | − | − |
| IOR/CAR | +++ | ++ | ND | − | − |
| IOR/CLB | +++ | +++ | ND | − | − |
| IOR/BER | +++ | + | ND | − | − |
| MM-83 | +++ | + | ND | − | − |
| RM-82 | ++ | +/− | ND | − | − |
| NT-68 | +++ | + | ND | − | − |
| STA-ET2.1 | +++ | ++ | ND | − | − |
| Osteosarcoma cells | | | | | |
| U2-OS | + | − | ++ | − | − |
| MG-63 | ++ | +/− | ND | − | − |
| IOR/OS7 | ++ | − | ND | − | − |
| MOS | ++ | − | ND | − | − |
| Leukaemic cells | | | | | |
| JURKAT | +++ | − | +++ | − | − |
| CCRF-CEM | +++ | − | +++ | − | − |
| HL-60 | +++ | − | +++ | − | − |
| MOLT-4 | +++ | − | +++ | − | − |
| Mesenchymal cells | | | | | |
| HSSC163 | + | − | ND | − | − |
| HSSC168 | ++ | − | ND | − | − |
| Blood cells | | | | | |
| PBMC | ++ | − | ++ | − | − |
| RBC | ND | − | +− | − | − |

Table 2 shows the level of reactivity of the scFvC7 antibody toward live/intact cells in comparison with other murine CD99 antibodies (mAb0662 and mAb013) and control antibodies scFvGO and IgG (non-specific mouse monoclonal).

Legend:
PBMC: peripheral blood mononuclear white cells;
RBC: red blood cells;
−, negative; +−, from 25 to 50%; +, from 50 to 75%; ++, from 75 to 100%; +++, 100% of cells positive but with a high level of fluorescence intensity;
ND: not determined.

The specificity of the human monoclonal antibody scFvC7 for Ewing sarcoma cells was also confirmed by immunohistochemical studies performed on tumour sections derived from patients. In these trials the scFvC7 antibody did not display any reactivity on various human tumours, including various types of osteosarcomas, whereas the only positive results were found on tissues of patients affected by Ewing sarcoma. The reasons for this selectivity of recognition may be of various origin. Those which seem most convincing are tied to the physicochemical and structural characteristics of the antibodies in scFv form (27-30 kDa); they can in fact intercept encrypted or masked epitopes usually inaccessible to immunoglobulins in the classic form (145-150 kDa). However, it cannot be ruled out that a possible reduced affinity of scFvC7 (sometimes observed in antibodies in scFv form) might represent a discriminating factor, by allowing the molecule in question to react only with cells that express high levels of CD99, as occurs in the case of Ewing sarcoma cells.

Antigens and Proteins

In order to isolate the human monoclonal antibody as a single-chain variable fragment (scFv) directed against the CD99 antigen present on the surface of human cells, three different recombinant proteins were used.

rCD99, corresponding to the deduced external domain within the range of amino acid residues 23-123 of the gene sequence of CD99 and genetically fused to the protein (CD99/GST), which was purchased from Abnova Corporation (Taipei, Taiwan).

CD99/GST was expressed in *E. coli* bacteria.

rCD99, corresponding to the deduced external domain within the range of amino acid residues 23-123 of the gene sequence of CD99 and genetically fused to the Fc region of the human IgG1 protein (CD99/Fc), which was purchased from R&D System (MN, USA).

CD99/FC was expressed in eukaryotic cells.

rCD99, corresponding to the deduced external domain within the range of amino acid residues 23-122, SEQ ID NO: 21 and encoded by the gene sequence of CD99 SEQ ID NO: 22, was genetically fused to 6 histidines (CD99/His) and was produced by the inventors, as described below in the paragraph "Expression and purification of CD99/His protein, used for the selection and screening of scFvC7".

The recombinant GST protein expressed in *E. coli* bacteria was purchased from Abnova (Taiwan).

ETH-2 Phage Antibody Library:

The ETH2 library of human synthetic recombinant antibodies consists in a vast series (more than $10^9$ antibody combinations) of scFv polypeptides displayed on the surface of the M13 phage.

The library was built thanks to random mutagenesis of the CDR3 of only 3 antibody gene segments of the germline (DP47 for the heavy chain, DPK22 and DPL 16 for the light chain).

The variability of the heavy chain was created by random mutagenesis of four-six positions of the CDR3 which replace the pre-existing positions 95-98. The diversity of the light chain was created by randomly mutagenizing six positions (96-101) of the CDR3(12).

Selection of scFv Directed Against rCD99:

5 mL immunotubes (Nunc, Maxisorp, DENMARK) were coated with GST protein in PBS at a concentration of 10 μg/mL and incubated overnight (ON), at 4° C.

After panning, the phages that did not bind to the antigen were recovered and used for the selection of scFv directed against the CD99 antigen using an immunotube previously incubated ON, at 4° C., with the CD99/GST antigen in PBS at a concentration of 10 μg/mL. The phages that did not specifically bind to the antigen were removed by numerous washes.

In accordance with Viti et al., (13) the phages bound to the antigen were diluted with 1 mL of 100 mM triethylamine and the solution was then immediately neutralized by adding 0.5 mL of Tris-HCl 1M, pH=7.4.

The eluted phages were used to infect the *E. coli* TG1 bacteria in the logarithmic phase of growth and amplified for the subsequent selection cycle.

In detail: a sufficient quantity of bacteria were inoculated into 50 mL of 2xTY with 100 μg/mL ampicillin and 1% glucose until arriving at an $OD_{600\ nm}$=0.05–0.1. The culture was made to grow to $OD_{600\ nm}$=0.4–0.5 and infected with the K07 helper phage in a phage/bacteria ratio of about 20:1. The recovered phages were concentrated by precipitation with PEG 6000 and used for the subsequent panning cycles (3-4 cycles are usually necessary to obtain an antigen-specific phage antibody from the ETH-2 library).

For the preparation of monoclonal phage antibodies, individual colonies of TG1 bacteria containing the phagemid were inoculated into 150 μL of 2xTY with 100 μg/mL ampicillin and 1% glucose in 96-well plates, incubated for 2 hrs at 37° C. and then again infected with $10^9$ cfu of K07 helper phage in 25 μl of 2xTY. After 30 min the plates were centrifuged at a speed of 1800 g for 10 min and the bacterial pellet was resuspended in 200 μL of 2xTY with 100 μg/mL ampicillin and 25 μg/mL kanamycin. The following day the plates were centrifuged at a speed of 1800 g for 10 min and the phage pellet was resuspended in PBS and then tested by ELISA.

ELISA:

96-well ELISA plates were coated with 50 μl/well of CD99/GST at a concentration of 10 μg/mL and incubated ON, at 4° C. The following day a blocking solution composed of 2% fat-free milk in PBS (MPBS) was added and after 2 hrs, the plates were washed with PBS containing 0.1% TWEEN 20 (TPBS). The plates were incubated for 2 hrs at room temperature (RT) with 50 μL of supernatant containing soluble scFv antibodies, anti-Flag M2 antibody (1:2000, Sigma Aldrich, MO, USA) and HRP-conjugated anti-mouse antibody (1:500, Dako, Glostrup, DENMARK).

In the ELISA assay performed using phage antibodies, the plates were incubated for 1 hr with the supernatant containing the phage antibodies and then incubated for 1 hr with HRP-conjugated anti-phage mouse antibody (1:1000, Amersham Pharmacia Biotec, Buckinghamshire, UK). All antibodies were resuspended in 2% MPBS. The reaction was visualized using 3,3'-5,5'-tetramethylbenzidine (BM blue, POD substrate, Roche Diagnostics; IN, USA) and stopped by adding 50 μl of 1M hydrosulfuric acid. The reaction was recorded using the ELISA reader (Biorad, CA, USA) and the results were read at a wavelength of 450 nm.

Purification of Soluble scFv:

For the production of soluble proteins in scFv format, *E. coli* TG1 cells were infected with specific phages and amplified at 37° C. in 2xTY containing 100 μg/mL ampicillin and 0.1% glucose until reaching an $OD_{600\ nm}$≥0.5. In order to induce the expression of antibodies, the cells were incubated ON at 30° C., after isopropyl-β-D-thiogalactopyranoside (IPTG)≥1 mM had been added to the culture.

Then the bacterial culture was centrifuged and the supernatant containing the scFv was collected.

The scFv antibodies were precipitated with ammonium sulfate and dialyzed in PBS. The scFv antibodies, tagged with a histidine tail, were purified by affinity chromatography on metal using agarose conjugated with $Ni^{2+}$ nitrilotriacetic acid (Qiagen Milan, Italy, EU). The scFv fragments were eluted with 250 mM imidazole in PBS, dialyzed, tested by ELISA for the specific recognition of the antigen and stored at −80° C.

Characterization of DNA and Sequences:

The plasmid DNAs encoding the specific scFv were digested with suitable endonucleases and the CDR3 regions were sequenced by means of an automated DNA sequencing machine (Biofab Research, Pomezia, Italy, EU) using the primers fdseq1 (SEQ ID NO: 26) and pelBback (SEQ ID NO: 27).

Cytofluorometry:

The expression of CD99 on cells was determined by cytofluorometry studies.

Intact/live human Ewing sarcoma cells and tumour cells of varying origin (see Table 2) were collected during the exponential phase of growth, washed, pelleted and resuspended in 2% MPBS. A total of $5 \times 10^5$ cells were incubated for 1 hr, at RT, in the presence of 5 ug/mL of scFv soluble protein; they were then centrifuged, washed abundantly and incubated with the secondary anti-Flag M2 antibody (25 μg/mL, Sigma) for 30 min, at 4° C.

The specific binding was revealed by incubating the cells for 30 min at 4° C. with a goat anti-mouse IgG conjugated to FITC (6 μg/mL, Pierce, IL, USA).

After marking the cell samples were washed, stored at 4° C. and immediately analyzed by FACS (Becton-Dickinson, NJ, USA).

Isolation and Cloning of the CD99 Gene mRNA was extracted from the Jurkat T-lymphoid cell line using the "QuickPrep Micro mRNA Purification Kit" (Amersham) and according to the manufacturer's instructions.

The mRNA (1 μg) was retrotranscribed using the "smart PCR Synthesis kit" (Clontech, CA, USA) in order to synthesize double-stranded cDNA.

The quality of the cDNA was analyzed by polymerase chain reaction (PCR) using specific primers for amplification of GAPDH, as the housekeeping gene.

The encoding sequence for the extracellular domain of CD99 was amplified by PCR with the primer CD99For (SEQ ID NO: 23) and the primer CD99Rev (SEQ ID NO: 24).

The sense primer contains the BamHI restriction site and the encoding sequence for the first six amino acids of the extracellular domain of CD99.

The antisense primer contains the encoding sequences for the final part of the extracellular domain of CD99 and the restriction site of the enzyme SalI.

The primers were designed on the basis of the nucleotide sequence of the gene MIC2 number NM_002414.3 (gi: 34147599) of the NCBI database. PCR was performed using the Pwo PCR enzyme (Roche Diagnostics) and the resulting PCR fragment was purified by agarose gel using the High Pure PCR Product Purification kit (Roche). The amplificate was digested with the restriction enzymes BamHI and SalI, and cloned in the plasmid pQE30Xa (Qiagen), containing the sequences for the six-histidine tag for purification of the protein. For the transformation with the recombinant plasmid the TG1 strain of *E. coli* was used and the transformed clones were analyzed by colony PCR. The positive clone was analyzed by automated DNA sequencing (Biofab Research).

Expression and Purification of the CD99/His Protein Used for the Selection and Screening of scFv C7:

The TG1 *E. coli* bacteria (supE hsdΔ5 thi Δ(lac-proAB) F' [traD36 proAB+ lacIqlacZΔM15]), transformed with the plasmid pQE30Xa CD99/His, were made to grow in 100 mL of 2xTY with 100 Δg/mL ampicillin and 0.1% glucose on a shaker, at 37° C., until reaching $OD_{600\,nm}=0.6$. IPTG (Sigma) was added at a final concentration of 1 mM. The bacteria were recovered 3 hrs later, centrifuged at 10,000 rpm for 20 min at 4° C. and lysed by sonication in lysis buffer (50 mM NaH2PO4, 300 mM NaCl, 10 mM imidazole, pH 8). The CD99/His protein was purified by affinity chromatography on Ni-NTA resin (Qiagen), using the protocol in native conditions according to the manufacturer's instructions.

The protein concentration was determined with the Fernandez-Patron method. The purified CD99/His protein was resuspended in PBS, aliquoted and stored at −80° C. The gene encoding the extracellular domain of CD99 (SEQ ID NO: 22) was amplified and inserted in the expression vector pQE30Xa, which contains the lac promotor for inducing expression of the protein and the sequence for the six-histidine tag for purification.

After transformation of the bacterial strain of TG1 *E. coli*, a number of clones were isolated and they demonstrated to be suitable for the production of CD99/His. The clone which showed the best protein induction was further characterized. The yield of purified protein was approximately 10 mg/L, using affinity chromatography on chelated metal.

The TG1 clones expressed only a 25 KDa protein rather than the 12 KDa protein detected by the commercial antibody 0662; the transformation was also effected with the amber codon non-suppressor bacterial strain TOP10, and the same result was obtained.

REFERENCES

1. Subbiah V, Anderson P, Lazar A J, Burdett E, Raymond K, Ludwig J A. Ewing's sarcoma: standard and experimental treatment options. Curr Treat Options Oncol 10, 126-140 (2009). Review
2. Scotlandi K. Targeted therapies in Ewing's sarcoma. Adv Exp Med. Biol. 587, 13-22 (2006) Review.
3. Picci P, Scotlandi K, Serra M, Rizzi A. Prognostic and therapeutic targets in the Ewing's family of tumors (PROTHETS). Adv Exp Med. Biol. 587, 1-12 (2006) Review
4. Alberti I, Bernard G, Rouquette-Jazdanian A K, Pelassy C, Pourtein M, Aussel C and Bernard A. CD99 isoforms expression dictates T cell functional outcomes. FASEB J 2002; 16: 1946-1948
5. Scotlandi K, Perdichizzi S, Bernard G, Nicoletti G, Nanni P, Lollini P L, Curti A, Manara M C, Benini S, Bernard A, Picci P: Targeting CD99 in association with doxorubicin: an effective combined treatment for Ewing's sarcoma. Eur J Cancer. 2006; 42(1):91-6
6. Mirick G R, Bradt B M, Denardo S J, Denardo G L: A review of human anti-globulin antibody (HAGA, HAMA, HACA, HAHA) responses to monoclonal antibodies. Not four letter words. Q J Nucl Med Mol. Imaging. 2004; 48(4):251-7
7. Liu X Y, Pop L M, Vitetta E S: Engineering therapeutic monoclonal antibodies. Immunol Rev. 2008; 222: 9-27. Review
8. Hinoda Y, Sasaki S, Ishida T, Imai K: Monoclonal antibodies as effective therapeutic agents for solid tumors. Cancer Sci. 2004; 95(8):621-5
9. Lanzavecchia A: Human monoclonal antibodies by immortalization of memory B cells. Curr Opin Biotechnol. 2007; 18(6):523-8
10. Carter P J: Potent antibody therapeutics by design. Nat Rev Immunol. 2006; 6(5):343-57
11. Hoogenboom H: Selecting and screening recombinant antibody libraries. Nat. Biotechnol. 2005; 23(9):1105-16
12. Holliger P, Hudson P J: Engineered antibody fragments and the rise of single domains. Nat Biotechnol. 2005; 23(9):1126-36
13. Sharkey R M and Goldenberg D M: Immunoconjugates Targeted Therapy of Cancer: New Prospects for Antibodies and cancer. CA Cancer J. Clin. 2006; 56; 226-243

14. Pavoni E, Flego M, Dupuis M L, Barca S, Petronzelli F, Anastasi A M, D'Alessio V, Pelliccia A, Vaccaro P, Monteriu G, Ascione A, De Santis R, Felici F, Cianfriglia M, Minenkova O.: Selection, affinity maturation, and characterization of a human scFv antibody against CEA protein. BMC Cancer 2006; 6:41-52
15. Kyeong C J, Nam H K, Weon S P, Seong H P, Youngmee B: The CD99 signal enhances Fas-mediated apoptosis in the human leukemic cell line, Jurkat. FEBS Letters 2003; 554: 478-484
16. Viti F, Nilsson F, Demartis S, Huber A, and Neri D: Design and use of phage display libraries for the selection of antibodies and enzymes. Methods Enzimol 2000; 326:480-505
17. Ames R S, Tornetta M A, Jones C S, and Ping Tsui: Isolation of neutralizing anti-05a monoclonal antibodies from a filamentous phage monovalent Fab display library. Journal of Immunology 1994; 152: 4572
18. Stausbol-Gron B, Wind T, Kjer S, Kahns L, Hansen N, Kristensen P, Clark B: A model phage display subtraction method with potential for analysis of differential gene expression. FEBS Letters 1996; 391:71-75
19. De Kruif J, Boel and Logtenberg T: Selection and application of human single-chain Fv antibody fragments from a semi-synthetic phage antibody display library with designed CDR3 regions. J. Mol. Biol. 1995; 248: 97-105
20. Carter P: Improving the efficacy of antibody-based cancer therapies. Nat Rev Cancer 2001; 1(2): 118-29

The invention claimed is:

1. A single-chain variable fragment (scFv), comprising:
   a heavy variable chain (VH);
   a light variable chain (VL); and
   a peptide linker joining said heavy variable chain to said light variable chain, wherein said fragment is directed against an epitope of the extracellular domain of the CD99 human protein consisting essentially of the amino acid sequence SEQ ID NO: 25 and wherein the VH chain comprises CDR1, CDR2 and CDR3 regions consisting essentially of amino acid sequences SEQ ID NO: 1, SEQ ID NO: 3 and SEQ ID NO: 4, respectively and the VL chain comprises CDR1, CDR2 and CDR3 regions consisting essentially of amino acid sequences SEQ ID NO: 2, SEQ ID NO: 5 and SEQ ID NO: 6, respectively.

2. The single-chain variable fragment according to claim 1, wherein said VH chain consists essentially of amino acid sequence SEQ ID NO: 7 or sequences having at least 95% identity.

3. The single-chain variable fragment according to claim 1, wherein said VL chain consists essentially of amino acid sequence SEQ ID NO: 8 or sequences having at least 95% identity.

4. The single-chain variable fragment according to claim 1, wherein said linker consists essentially of amino acid sequence SEQ ID NO: 9.

5. The single-chain variable fragment according to claim 1, wherein said fragment consists essentially of SEQ ID NO: 10 or sequences having at least 95% identity.

6. An artificial nucleotide sequence encoding a single chain variable fragment according to claim 1.

7. The nucleotide sequence according to claim 6, consisting essentially of SEQ ID NO: 20 or nucleotide sequences derived therefrom as a result of degeneration of the genetic code.

8. An expression vector comprising a nucleotide sequence according to claim 6 or 7.

9. A host cell comprising an expression vector according to claim 8.

10. A human, humanized or chimeric antibody directed against an epitope of the extracellular domain of the CD99 human protein consisting essentially of the amino acid sequence SEQ ID NO: 25 wherein said antibody has the VH chain comprising CDR1, CDR2 and CDR3 regions consisting essentially of amino acid sequences SEQ ID NO: 1, SEQ ID NO: 3 and SEQ ID NO: 4, respectively and the VL chain comprising CDR1, CDR2 and CDR3 regions consisting essentially of amino acid sequences SEQ ID NO: 2, SEQ ID NO: 5 and SEQ ID NO: 6, respectively.

11. An antibody fragment directed against an epitope of the extracellular domain of the CD99 human protein consisting essentially of the amino acid sequence SEQ ID NO: 25 and wherein said fragment has the VH chain comprising CDR1, CDR2 and CDR3 regions consisting essentially of amino acid sequences SEQ ID NO: 1, SEQ ID NO: 3 and SEQ ID NO: 4, respectively and the VL chain comprising CDR1, CDR2 and CDR3 regions consisting essentially of amino acid sequences SEQ ID NO: 2, SEQ ID NO: 5 and SEQ ID NO: 6, respectively.

12. A method of treating Ewing sarcoma comprising a step of administering to a patient in need of such treatment a therapeutically effective amount of the single-chain variable fragment according to claim 1, alone or in combination with chemotherapy drugs and/or radiotherapy and/or surgical resection said Ewing sarcoma expressing the extracellular domain of the CD99 human protein consisting essentially of the amino acid sequence SEQ ID NO: 25.

13. An immunodiagnostic kit for the detection of CD99 human protein, said kit comprising the antibody fragment according to claim 1.

14. The host cell according to claim 9, wherein the cell is a bacterium.

15. The host cell according to claim 14, wherein the bacterium is *Escherichia coli*.

16. A method of treating Ewing sarcoma comprising a step of administering to a patient in need of such treatment a therapeutically effective amount of the human, humanized or chimeric antibody according to claim 10, alone or in combination with chemotherapy drugs and/or radiotherapy and/or surgical resection said Ewing sarcoma expressing the extracellular domain of the CD99 human protein consisting essentially of the amino acid sequence SEQ ID NO: 25.

17. A method of treating Ewing sarcoma comprising a step of administering to a patient in need of such treatment a therapeutically effective amount of the antibody fragment according to claim 11, alone or in combination with chemotherapy drugs and/or radiotherapy and/or surgical resection said Ewing sarcoma expressing the extracellular domain of the CD99 human protein consisting essentially of the amino acid sequence SEQ ID NO: 25.

18. A method of delivering into cancer cells expressing an epitope of the extracellular domain of the CD99 human protein consisting essentially of the amino acid sequence SEQ ID NO: 25 a cytotoxic compound, a radionuclide, a lymphokine or a chemokine comprising a step of administering to the cancer cells said cytotoxic compound, said radionuclide, said lymphokine or said chemokine conjugated to the single-chain variable fragment according to claim 1.

19. A method of delivering into cancer cells expressing an epitope of the extracellular domain of the CD99 human protein consisting essentially of the amino acid sequence SEQ ID NO: 25 a cytotoxic compound, a radionuclide, a lymphokine or a chemokine comprising a step of administering to the cancer cells said cytotoxic compound, said radionuclide, said lymphokine or said chemokine conjugated to the human, humanized or chimeric antibody according to claim 10.

20. A method of delivering into cancer cells expressing an epitope of the extracellular domain of the CD99 human protein consisting essentially of the amino acid sequence SEQ ID NO: 25 a cytotoxic compound, a radionuclide, a lymphokine or a chemokine comprising a step of administering to the cancer cells said cytotoxic compound, said radionuclide, said lymphokine or said chemokine conjugated to the antibody fragment according to claim 11.

21. An immunodiagnostic kit for the detection of CD99 human protein, said kit comprising the human, humanized or chimeric antibody according to claim 10.

22. The kit according to claim 13 for the diagnosis of Ewing sarcoma.

23. An immunodiagnostic kit for the detection of CD99 human protein, said kit comprising the antibody fragment according to claim 11.

24. The kit according to claim 21 for the diagnosis of Ewing sarcoma.

25. The kit according to claim 23 for the diagnosis of Ewing sarcoma.

26. A diabody directed against an epitope of the extracellular domain of the CD99 human protein consisting essentially of the amino acid sequence SEQ ID NO: 25 and having a VH chain with CDR1, CDR2 and CDR3 regions consisting essentially of amino acid sequences SEQ ID NO: 1, SEQ ID NO: 3 and SEQ ID NO: 4, respectively and a VL chain with CDR1, CDR2 and CDR3 regions consisting essentially of amino acid sequences SEQ ID NO: 2, SEQ ID NO: 5 and SEQ ID NO: 6, respectively.

* * * * *

UNITED STATES PATENT AND TRADEMARK OFFICE
CERTIFICATE OF CORRECTION

PATENT NO. : 8,710,194 B2
APPLICATION NO. : 13/509276
DATED : April 29, 2014
INVENTOR(S) : Picci et al.

It is certified that error appears in the above-identified patent and that said Letters Patent is hereby corrected as shown below:

Title Page, item (73) Assignee
    Istituto Ortopedico Rizzoli, Bologna (IL) should read "Istituto Ortopedico Rizzoli, Bologna (IT)"

Title Page, item (73) Assignee
    Please add the additional Assignee:
    "Istituto Superiore Sanita', Roma (IT)"

Signed and Sealed this
Twenty-eighth Day of April, 2015

Michelle K. Lee
*Director of the United States Patent and Trademark Office*